(12) United States Patent
Sun et al.

(10) Patent No.: US 6,797,493 B2
(45) Date of Patent: Sep. 28, 2004

(54) FC FUSION PROTEINS OF HUMAN GRANULOCYTE COLONY-STIMULATING FACTOR WITH INCREASED BIOLOGICAL ACTIVITIES

(76) Inventors: Lee-Hwei K. Sun, 4212 Villanova St., Houston, TX (US) 77005; Bill N. C. Sun, 4901 Welford, Bellaire, TX (US) 77401; Cecily R. Y. Sun, 4901 Welford, Bellaire, TX (US) 77401

( * ) Notice: Subject to any disclaimer, the term of this patent is extended or adjusted under 35 U.S.C. 154(b) by 215 days.

(21) Appl. No.: 09/968,362

(22) Filed: Oct. 1, 2001

(65) Prior Publication Data

US 2003/0082679 A1 May 1, 2003

(51) Int. Cl.[7] .................... C07K 16/00; C07K 14/00; C12N 5/10
(52) U.S. Cl. .................. 435/69.7; 435/325; 435/358; 530/350
(58) Field of Search .................. 530/350; 435/325, 435/358, 69.7

(56) References Cited

U.S. PATENT DOCUMENTS

| | | | |
|---|---|---|---|
| 5,116,964 A | 5/1992 | Capon et al. | 536/27 |
| 5,349,053 A | 9/1994 | Landolfi | 530/351 |
| 5,723,125 A | 3/1998 | Chang et al. | 424/134.1 |
| 5,876,969 A * | 3/1999 | Fleer et al. | 435/69.7 |
| 6,204,007 B1 | 3/2001 | Owens et al. | 435/69.1 |
| 6,242,195 B1 | 6/2001 | Idusogie et al. | 435/7.1 |
| 6,291,661 B1 * | 9/2001 | Graddis et al. | 536/23.4 |

OTHER PUBLICATIONS

Ashkenazi and Chamow, "Immunoadhesins as research tools and therapeutic agents" Current Opinion in Immunology, 9, pp 195–200 (1997).
Jefferis et al., "IgG–Fc–mediated effector definition of interaction sites for effector functions: molecular definition of interaction sites for effector ligands and the role of glycosylation" Immunoogica Reviews, 163, pp 59–76 (1998).
Hutchins, et al., "Improved biodistribution, tumor targeting, and reduced immunogenicity in mice with a & 4 variant of Campath–1H", Proceedings National Academy of Sciences, USA, 92, pp 11980–11984 (1995).
Duncan et al., "The binding site for C1q on IgG" Nature, 332, pp 738–740 (1988).

* cited by examiner

Primary Examiner—Elizabeth Kemmerer
(74) Attorney, Agent, or Firm—Hsiang-ning Sun

(57) ABSTRACT

Fc fusion proteins of human G-CSF with increased biological activities relative to rhG-CSF on a molar basis are disclosed. The hG-CSF-L-vFc fusion protein comprises hG-CSF, a flexible peptide linker of about 20 or fewer amino acids, and a human IgG Fc variant. The Fc variant is of a non-lytic nature and shows minimal undesirable Fc-mediated side effects. A method is also disclosed to make or produce such fusion proteins at high expression levels. Such hG-CSF-L-vFc fusion proteins exhibit extended serum half-life and increased biological activities, leading to improved pharmacokinetics and pharmacodynamics, thus fewer injections will be needed within a period of time.

12 Claims, 4 Drawing Sheets

Amino acid sequence alignment in human IgG isotypes and their variants.

| Human IgG Isotype | Amino Acid Position | | | | | |
|---|---|---|---|---|---|---|
| | 228......234 | 235 | 236 | 237......330 | 331 |
| G1 | Pro......Leu | Leu | Gly | Gly......Ala | Pro |
| G2 | Pro......Val | Ala | ......... | Gly......Ala | Pro |
| G4 | Ser......Phe | Leu | Gly | Gly......Ser | Ser |
| G1 variant | Pro......Val | Ala | Gly | Gly......Ala | Ser |
| G2 variant | Pro......Val | Ala | ......... | Gly......Ala | Ser |
| G4 variant | Pro......Phe | Ala | Gly | Gly......Ser | Ser |

| ID number | Corresponding Row |
|---|---|
| SEQ ID NO:26 | G1 |
| SEQ ID NO:27 | G2 |
| SEQ ID NO:28 | G4 |
| SEQ ID NO:22 | G1 variant |
| SEQ ID NO:18 | G2 variant |
| SEQ ID NO:20 | G4 variant |

Amino acid sequence alignment in human IgG isotypes and their variants.

| Human IgG Isotype | Amino Acid Position | | | | | |
|---|---|---|---|---|---|---|
| | 228......234 | 235 | 236 | 237......330 | 331 |
| G1 | Pro......Leu | Leu | Gly | Gly......Ala | Pro |
| G2 | Pro......Val | Ala | ......... | Gly......Ala | Pro |
| G4 | Ser......Phe | Leu | Gly | Gly......Ser | Ser |
| G1 variant | Pro......Val | Ala | Gly | Gly......Ala | Ser |
| G2 variant | Pro......Val | Ala | ......... | Gly......Ala | Ser |
| G4 variant | Pro......Phe | Ala | Gly | Gly......Ser | Ser |

| ID number | Corresponding Row |
|---|---|
| SEQ ID NO:26 | G1 |
| SEQ ID NO:27 | G2 |
| SEQ ID NO:28 | G4 |
| SEQ ID NO:22 | G1 variant |
| SEQ ID NO:18 | G2 variant |
| SEQ ID NO:20 | G4 variant |

*FIG. 1*

DNA and deduced amino acid sequences of hG-CSF-L-vFc$_{\gamma 2}$

DNA  SEQ ID NO: 17
Amino Acid Sequence  SEQ ID NO: 18

```
aag ctt ccc aga ccc atg gct gga cct gcc acc cag agc ccc atg aag ctg atg gcc ctg      60
HindIII           M   A   G   P   A   T   Q   S   P   M   K   L   M   A   L
                 -30                                              -20
cag ctg ctg ctg tgg cac agt gca ctc tgg aca gtg cag gaa gcc acc ccc ctg ggc cct     120
 Q   L   L   L   W   H   S   A   L   W   T   V   Q   E   A   T   P   L   G   P
                -10                                      -1   1
gcc agc tcc ctg ccc cag agc ttc ctg ctc aag tgc tta gag caa gtg agg aag atc cag     180
 A   S   S   L   P   Q   S   F   L   L   K   C   L   E   Q   V   R   K   I   Q
                10                                       20
ggc gat ggc gca gcg ctc cag gag aag ctg tgt gcc acc tac aag ctg tgc cac ccc gag     240
 G   D   G   A   A   L   Q   E   K   L   C   A   T   Y   K   L   C   H   P   E
                30                                       40
gag ctg gtg ctg ctc gga cac tct ctg ggc atc ccc tgg gct ccc ctg agc agc tgc ccc     300
 E   L   V   L   L   G   H   S   L   G   I   P   W   A   P   L   S   S   C   P
                50                                       60
agc cag gcc ctg cag ctg gca ggc tgc ttg agc caa ctc cat agc ggc ctt ttc ctc tac     360
 S   Q   A   L   Q   L   A   G   C   L   S   Q   L   H   S   G   L   F   L   Y
                70                                       80
cag ggg ctc ctg cag gcc ctg gaa ggg atc tcc ccc gag ttg ggt ccc acc ttg gac aca     420
 Q   G   L   L   Q   A   L   E   G   I   S   P   E   L   G   P   T   L   D   T
                90                                      100
ctg cag ctg gac gtc gcc gac ttt gcc acc acc atc tgg cag cag atg gaa gaa ctg gga     480
 L   Q   L   D   V   A   D   F   A   T   T   I   W   Q   Q   M   E   E   L   G
               110                                      120
atg gcc cct gcc ctg cag ccc acc cag ggt gcc atg ccg gcc ttc gcc tct gct ttc cag     540
 M   A   P   A   L   Q   P   T   Q   G   A   M   P   A   F   A   S   A   F   Q
               130                                      140
cgc cgg gca gga ggg gtc cta gtt gcc tcc cat ctg cag agc ttc ctg gag gtg tcg tac     600
 R   R   A   G   G   V   L   V   A   S   H   L   Q   S   F   L   E   V   S   Y
               150                                      160
cgc gtt cta cgc cac ctt gcc cag ccc gga tcc ggt ggc ggt tcc ggt gga ggc gga agc     660
 R   V   L   R   H   L   A   Q   P   G   S   G   G   G   S   G   G   G   S
               170                                      180
ggc ggt gga gga tca gag cgc aaa tgt tgt gtc gag tgc cca ccg tgc cca gca cca cct     720
 G   G   G   S   E   R   K   C   C   V   E   C   P   P   C   P   A   P   P
               190                                      200
gtg gca gga ccg tca gtc ttc ctc ttc ccc cca aaa ccc aag gac acc ctc atg atc tcc     780
 V   A   G   P   S   V   F   L   F   P   P   K   P   K   D   T   L   M   I   S
               210                                      220
cgg acc cct gag gtc acg tgc gtg gtg gtg gac gtg agc cac gaa gac ccc gag gtc cag     840
 R   T   P   E   V   T   C   V   V   V   D   V   S   H   E   D   P   E   V   Q
               230                                      240
ttc aac tgg tac gtg gac ggc gtg gag gtg cat aat gcc aag aca aag cca cgg gag gag     900
 F   N   W   Y   V   D   G   V   E   V   H   N   A   K   T   K   P   R   E   E
               250                                      260
cag ttc aac agc acg ttc cgt gtg gtc agc gtc ctc acc gtt gtg cac cag gac tgg ctg     960
 Q   F   N   S   T   F   R   V   V   S   V   L   T   V   V   H   Q   D   W   L
               270                                      280
aac ggc aag gag tac aag tgc aag gtc tcc aac aaa ggc ctc cca gcc tcc atc gag aaa    1020
 N   G   K   E   Y   K   C   K   V   S   N   K   G   L   P   A   S   I   E   K
               290                                      300
acc atc tcc aaa acc aaa ggg cag ccc cga gaa cca cag gtg tac acc ctg ccc cca tcc    1080
 T   I   S   K   T   K   G   Q   P   R   E   P   Q   V   Y   T   L   P   P   S
               310                                      320
cgg gag gag atg acc aag aac cag gtc agc ctg acc tgc ctg gtc aaa ggc ttc tac ccc    1140
 R   E   E   M   T   K   N   Q   V   S   L   T   C   L   V   K   G   F   Y   P
               330                                      340
agc gac atc gcc gtg gag tgg gag agc aat ggg cag ccg gag aac aac tac aag acc aca    1200
 S   D   I   A   V   E   W   E   S   N   G   Q   P   E   N   N   Y   K   T   T
               350                                      360
cct ccc atg ctg gac tcc gac ggc tcc ttc ttc ctc tac agc aag ctc acc gtg gac aag    1260
 P   P   M   L   D   S   D   G   S   F   F   L   Y   S   K   L   T   V   D   K
               370                                      380
agc agg tgg cag cag ggg aac gtc ttc tca tgc tcc gtg atg cat gag gct ctg cac aac    1320
 S   R   W   Q   Q   G   N   V   F   S   C   S   V   M   H   E   A   L   H   N
               390                                      400
cac tac acg cag aag agc ctc tcc ctg tct ccg ggt aaa tga gaa ttc                    1368
 H   Y   T   Q   K   S   L   S   L   S   P   G   K      EcoRI
               410                             418
```

*FIG. 2A*

DNA and deduced amino acid sequences of hG-CSF-L-vFc$_{\gamma4}$

DNA                SEQ ID NO:    19
Amino Acid Sequence  SEQ ID NO:  20

```
aag ctt ccc aga ccc atg gct gga cct gcc acc cag agc ccc atg aag ctg atg gcc ctg    60
HindIII             M   A   G   P   A   T   Q   S   P   M   K   L   M   A   L
                   -30                                     -20 cag ctg ctg ctg tgg cac agt gca ctc tgg aca gtg cag gaa gcc acc ccc ctg ggc cct   120
 Q   L   L   L   W   H   S   A   L   W   T   V   Q   E   A   T   P   L   G   P
               -10                                     -1   1 gcc agc tcc ctg ccc cag agc ttc ctg ctc aag tgc tta gag caa gtg agg aag atc cag   180
 A   S   S   L   P   Q   S   F   L   L   K   C   L   E   Q   V   R   K   I   Q
                10                                      20 ggc gat ggc gca gcg ctc cag gag aag ctg tgt gcc acc tac aag ctg tgc cac ccc gag   240
 G   D   G   A   A   L   Q   E   K   L   C   A   T   Y   K   L   C   H   P   E
                30                                      40 gag ctg gtg ctg ctc gga cac tct ctg ggc atc ccc tgg gct ccc ctg agc agc tgc ccc   300
 E   L   V   L   L   G   H   S   L   G   I   P   W   A   P   L   S   S   C   P
                50                                      60 agc cag gcc ctg cag ctg gca ggc tgc ttg agc caa ctc cat agc ggc ctt ttc ctc tac   360
 S   Q   A   L   Q   L   A   G   C   L   S   Q   L   H   S   G   L   F   L   Y
                70                                      80 cag ggg ctc ctg cag gcc ctg gaa ggg atc tcc ccc gag ttg ggt ccc acc ttg gac aca   420
 Q   G   L   L   Q   A   L   E   G   I   S   P   E   L   G   P   T   L   D   T
                90                                     100 ctg cag ctg gac gtc gcc gac ttt gcc acc acc atc tgg cag cag atg gaa gaa ctg gga   480
 L   Q   L   D   V   A   D   F   A   T   T   I   W   Q   Q   M   E   E   L   G
               110                                     120 atg gcc cct gcc ctg cag ccc acc cag ggt gcc atg ccg gcc ttc gcc tct gct ttc cag   540
 M   A   P   A   L   Q   P   T   Q   G   A   M   P   A   F   A   S   A   F   Q
               130                                     140 cgc cgg gca gga ggg gtc cta gtt gcc tcc cat ctg cag agc ttc ctg gag gtg tcg tac   600
 R   R   A   G   G   V   L   V   A   S   H   L   Q   S   F   L   E   V   S   Y
               150                                     160 cgc gtt cta cgc cac ctt gcc cag ccc gga tcc ggt ggt tcc ggt gga ggc gga agc       660
 R   V   L   R   H   L   A   Q   P   G   S   G   G   S   G   G   G   S
               170                                     180 ggc ggt gga gga tca gag tcc aaa tat ggt ccc cca tgc cca gca tgc cca gca cct gag   720
 G   G   G   G   S   E   S   K   Y   G   P   P   C   P   A   C   P   A   P   E
               190                                     200 ttc gcg ggg gga cca tca gtc ttc ctg ttc ccc cca aaa ccc aag gac act ctc atg atc   780
 F   A   G   G   P   S   V   F   L   F   P   P   K   P   K   D   T   L   M   I
               210                                     220 tcc cgg acc cct gag gtc acg tgc gtg gtg gtg gac gtg agc cag gaa gac ccc gag gtc   840
 S   R   T   P   E   V   T   C   V   V   V   D   V   S   Q   E   D   P   E   V
               230                                     240 cag ttc aac tgg tac gtg gat ggc gtg gag gtg cat aat gcc aag aca aag ccg cgg gag   900
 Q   F   N   W   Y   V   D   G   V   E   V   H   N   A   K   T   K   P   R   E
               250                                     260 gag cag ttc aac agc acg tac cgt gtg gtc agc gtc ctc acc gtc ctg cac cag gac tgg   960
 E   Q   F   N   S   T   Y   R   V   V   S   V   L   T   V   L   H   Q   D   W
               270                                     280 ctg aac ggc aag gag tac aag tgc aag gtc tcc aac aaa ggc ctc ccg tcc tcc atc gag  1020
 L   N   G   K   E   Y   K   C   K   V   S   N   K   G   L   P   S   S   I   E
               290                                     300 aaa acc atc tcc aaa gcc aaa ggg cag ccc cga gag cca cag gtg tac acc ctg ccc cca  1080
 K   T   I   S   K   A   K   G   Q   P   R   E   P   Q   V   Y   T   L   P   P
               310                                     320 tcc cag gag gag atg acc aag aac cag gtc agc ctg acc tgc ctg gtc aaa ggc ttc tac  1140
 S   Q   E   E   M   T   K   N   Q   V   S   L   T   C   L   V   K   G   F   Y
               330                                     340 ccc agc gac atc gcc gtg gag tgg gag agc aat ggg cag ccg gag aac aac tac aag acc  1200
 P   S   D   I   A   V   E   W   E   S   N   G   Q   P   E   N   N   Y   K   T
               350                                     360 acg cct ccc gtg ctg gac tcc gac ggc tcc ttc ttc ctc tac agc agg cta acc gtg gac  1260
 T   P   P   V   L   D   S   D   G   S   F   F   L   Y   S   R   L   T   V   D
               370                                     380 aag agc agg tgg cag gag ggg aat gtc ttc tca tgc tcc gtg atg cat gag gct ctg cac  1320
 K   S   R   W   Q   E   G   N   V   F   S   C   S   V   M   H   E   A   L   H
               390                                     400 aac cac tac aca cag aag agc ctc tcc ctg tct ctg ggt aaa tga gaa ttc              1371
 N   H   Y   T   Q   K   S   L   S   L   S   L   G   K       EcoRI
               410                             419
```

FIG. 2B

DNA and deduced amino acid sequences of hG-CSF-L-vFc$_{\gamma1}$

| | |
|---|---|
| DNA | SEQ ID NO: 21 |
| Amino Acid Sequence | SEQ ID NO: 22 |

```
aag ctt ccc aga ccc atg gct gga cct gcc acc cag agc ccc atg aag ctg atg gcc ctg    60
HindIII               M   A   G   P   A   T   Q   S   P   M   K   L   M   A   L
                     -30                                 -20
cag ctg ctg ctg tgg cac agt gca ctc tgg aca gtg cag gaa gcc acc ccc ctg ggc cct   120
 Q   L   L   L   W   H   S   A   L   W   T   V   Q   E   A   T   P   L   G   P
                 -10                                  -1   1
gcc agc tcc ctg ccc cag agc ttc ctg ctc aag tgc tta gag caa gtg agg aag atc cag   180
 A   S   S   L   P   Q   S   F   L   L   K   C   L   E   Q   V   R   K   I   Q
                 10                                  20
ggc gat ggc gca gcg ctc cag gag aag ctg tgt gcc acc tac aag ctg tgc cac ccc gag   240
 G   D   G   A   A   L   Q   E   K   L   C   A   T   Y   K   L   C   H   P   E
                 30                                  40
gag ctg gtg ctg ctc gga cac tct ctg ggc atc ccc tgg gct ccc ctg agc agc tgc ccc   300
 E   L   V   L   L   G   H   S   L   G   I   P   W   A   P   L   S   S   C   P
                 50                                  60
agc cag gcc ctg cag ctg gca ggc tgc ttg agc caa ctc cat agc ggc ctt ttc ctc tac   360
 S   Q   A   L   Q   L   A   G   C   L   S   Q   L   H   S   G   L   F   L   Y
                 70                                  80
cag ggg ctc ctg cag gcc ctg gaa ggg atc tcc ccc gag ttg ggt ccc acc ttg gac aca   420
 Q   G   L   L   Q   A   L   E   G   I   S   P   E   L   G   P   T   L   D   T
                 90                                 100
ctg cag ctg gac gtc gcc gac ttt gcc acc acc atc tgg cag cag atg gaa gaa ctg gga   480
 L   Q   L   D   V   A   D   F   A   T   T   I   W   Q   Q   M   E   E   L   G
                110                                 120
atg gcc cct gcc ctg cag ccc acc cag ggt gcc atg ccg gcc ttc gcc tct gct ttc cag   540
 M   A   P   A   L   Q   P   T   Q   G   A   M   P   A   F   A   S   A   F   Q
                130                                 140
cgc cgg gca gga ggg gtc cta gtt gcc tcc cat ctg cag agc ttc ctg gag gtg tcg tac   600
 R   R   A   G   G   V   L   V   A   S   H   L   Q   S   F   L   E   V   S   Y
                150                                 160
cgc gtt cta cgc cac ctt gcc cag ccc gga tcc ggt ggc ggt tcc ggt gga ggc gga agc   660
 R   V   L   R   H   L   A   Q   P   G   S   G   G   G   S   G   G   G   G   S
                170                                 180
ggc ggt gga gga tca gac aaa act cac aca tgc cca ccg tgc cca gca cct gaa gtc gcg   720
 G   G   G   G   S   D   K   T   H   T   C   P   P   C   P   A   P   E   V   A
                190                                 200
ggg gga ccg tca gtc ttc ctc ttc ccc cca aaa ccc aag gac acc ctc atg atc tcc cgg   780
 G   G   P   S   V   F   L   F   P   P   K   P   K   D   T   L   M   I   S   R
                210                                 220
aca cct gag gtc aca tgc gtg gtg gtg gac gtg agc cac gaa gac cct gag gtc aag ttc   840
 T   P   E   V   T   C   V   V   V   D   V   S   H   E   D   P   E   V   K   F
                230                                 240
aac tgg tac gtg gac ggc gtg gag gtg cat aat gcc aag aca aag ccg cgg gag gag cag   900
 N   W   Y   V   D   G   V   E   V   H   N   A   K   T   K   P   R   E   E   Q
                250                                 260
tac aac agc acg tac cgg gtg gtc agc gtc ctc acc gtc ctg cac cag gac tgg ctg aat   960
 Y   N   S   T   Y   R   V   V   S   V   L   T   V   L   H   Q   D   W   L   N
                270                                 280
ggc aag gag tac aag tgc aag gtc tcc aac aaa gcc ctc cca gcc tcc atc gag aaa acc  1020
 G   K   E   Y   K   C   K   V   S   N   K   A   L   P   A   S   I   E   K   T
                290                                 300
atc tcc aaa gcc aaa ggg cag ccc cga gaa cca cag gtg tac acc ctg ccc cca tcc cgg  1080
 I   S   K   A   K   G   Q   P   R   E   P   Q   V   Y   T   L   P   P   S   R
                310                                 320
gat gag ctg acc aag aac cag gtc agc ctg acc tgc ctg gtc aaa ggc ttc tat ccc agc  1140
 D   E   L   T   K   N   Q   V   S   L   T   C   L   V   K   G   F   Y   P   S
                330                                 340
gac atc gcc gtg gag tgg gag agc aat ggg cag ccg gag aac aac tac aag acc acg cct  1200
 D   I   A   V   E   W   E   S   N   G   Q   P   E   N   N   Y   K   T   T   P
                350                                 360
ccc gtg ctg gac tcc gac ggc tcc ttc ttc ctc tac agc aag ctc acc gtg gac aag agc  1260
 P   V   L   D   S   D   G   S   F   F   L   Y   S   K   L   T   V   D   K   S
                370                                 380
agg tgg cag cag ggg aac gtc ttc tca tgc tcc gtg atg cat gag gct ctg cac aac cac  1320
 R   W   Q   Q   G   N   V   F   S   C   S   V   M   H   E   A   L   H   N   H
                390                                 400
tac acg cag aag agc ctc tcc ctg tct ccg ggt aaa tga gaa ttc                       1365
 Y   T   Q   K   S   L   S   L   S   P   G   K       EcoRI
                410                             417
```

*FIG. 2C*

FC FUSION PROTEINS OF HUMAN GRANULOCYTE COLONY-STIMULATING FACTOR WITH INCREASED BIOLOGICAL ACTIVITIES

BACKGROUND

Granulocyte colony-stimulating factor (G-CSF) is a 20 kilodalton (kDa) glycoprotein that promotes the proliferation of progenitor cells and induces their differentiation into neutrophils. In addition, G-CSF prolongs the survival of mature neutrophils and activates their functions Human G-CSF (hG-CSF) is produced by monocytes, macrophages, fibroblasts and endothelial cells (see, for example, Moore, *Annu. Rev. Immunol*, 9:159–191, 1991; Nicola, *Annu. Rev. Biochem.*, 58:45–77, 1991). The biological effects of G-CSF are mediated through its interaction with the G-CSF receptor (G-CSF-Rc) expressed on the surface of bone marrow hematopoietic progenitors and cells of the myeloid lineage. Upon binding G-CSF, the receptor is activated and undergoes homodimerization, followed by phosphorylation of Janus family of tyrosine kinases. Subsequently, a series of intracellular signal transduction events take place, leading to the increase of the number of progenitor cells, their maturation into neutrophils, and further activation of effector functions in mature neutrophils (see, for example, Demetri et al., *Blood*, 78:2791–2808, 1991). Therefore, G-CSF plays an essential role not only in the regulation and maintenance of hematopoiesis, but also in host defense against infection and inflammation.

Recombinant human G-CSF (rhG-CSF) is widely used in the treatment of patients with neutropenia as a result of receiving chemotherapy. Administration of rhG-CSF is effective in restoring functioning neutrophils to these patients, leading to a decrease of infection-related events. Use of rhG-CSF allows intensified dosing or scheduling of chemotherapeutic agents that may be of benefit to cancer patients. Besides chemotherapy-induced neutropenia, rhG-CSF has been used for the treatment of myelosuppression after bone marrow transplantation, acute leukemia, aplastic anemia, myelodysplastic syndrome, severe chronic neutropenias, and mobilization of peripheral blood progenitor cells for transplantation (see, for example, Welte et al., *Blood*, 88:1907–1929, 1996).

The elimination half-life of the serum concentration of rhG-CSF is approximately 3 to 4 h for intravenous or subcutaneous administration. The safety profile and patient tolerance of rhG-CSF are good with medullary bone pain being the only frequent and significant side effect. The relatively low toxicity of rhG-CSF has made it feasible to develop longer-acting derivatives to decrease the inconvenience of the daily or twice-daily injection schedule. Attachment of polyethylene glycol (PEG) to various proteins, including G-CSF, has been reported to yield derivatives with higher in vivo potency due to their longer half-lives (see, for example, Zalipsky et al., in *"PEG chemistry: biotechnical and biomedical applications"*, pp. 347–370, 1992). PEG-conjugated proteins usually have considerably lower in vitro biological activity than their unmodified parent proteins (Eliason et al., *Stem Cells*, 18:40–45, 2000). The increased in vivo potency of these modified proteins is, at least in part, due to decreased removal by the kidney in a manner proportional to their molecular weight (Yamaoda et al., *J. Pharmaceut. Sci.*, 83:601–606, 1994). We unexpectedly discover that it is possible to increase the potency of hG-CSF through prolonging its half-life as well as enhancing its biological activity is to attach the Fc region derived from human IgG at the C-terminus of hG-CSF, as described in this invention.

Immunoglobulins of IgG class are among the most abundant proteins in human blood. Their circulation half-lives can reach as long as 21 days. Fusion proteins have been reported to combine the Fc regions of IgG with the domains of another protein, such as various cytokines and soluble receptors (see, for example, Capon et al., *Nature*, 337:525–531, 1989; Chamow et al., *Trends Biotechnol.*, 14:52–60, 1996); U.S. Pat. Nos. 5,116,964 and 5,541,087). The prototype fusion protein is a homodimeric protein linked through cysteine residues in the hinge region of IgG Fc, resulting in a molecule similar to an IgG molecule without the CHI domains and light chains. Due to the structural homology, Fc fusion proteins exhibit in vivo pharmacokinetic profile comparable to that of human IgG with a similar isotype. This approach has been applied to several therapeutically important cytokines, such as IL-2 and IFN-$\alpha_{2a}$, and soluble receptors, such as TNF-Rc and IL-5-Rc (see, for example, U.S. Pat. Nos. 5,349,053 and 6,224,867). It is desirable to extend the circulating half-life of G-CSF and/or to increase its biological activity by making fusion proteins containing G-CSF linked to the Fc portion of the human IgG protein as disclosed and/or described in this invention.

Erythropoietin (EPO) derivatives, such as dimers, have been reported. Relative to the EPO monomer, a fusion protein consisting of two complete EPO domains separated by a 3- to 7-amino acid peptide linker exhibited reduced activity (Qiu et al., *J. Biol. Chem.*, 273:11173–11176, 1998). However, when the peptide linker between the two EPO domains was 17 amino acids in length, the dimeric EPO molecule exhibited considerably enhanced in vitro and in vivo activities (see, for example, Sytkowski et al., *J. Biol. Chem.*, 274:24773–24778, 1999; U.S. Pat. No. 6,187,564). The length of the peptide linker between the two hematopoietic growth factors is important, while not bound by this theory, presumably due to its effect on the flexibility of such molecular forms. We find that this approach is generally applicable to other therapeutic proteins, including G-CSF. We'll also refer this to this as a flexible peptide linker.

In most of the reported Fc fusion protein molecules, a hinge region serves as a spacer between the Fc region and the cytokine or soluble receptor at the amino-terminus, allowing these two parts of the molecule to function separately (see, for example, Ashkenazi et al., *Current Opinion in Immunology*, 9:195–200, 1997). A human G-CSF fusion protein with an appropriate peptide linker between the hG-CSF and Fc moieties (hG-CSF-L-Fc) is more active than rhG-CSF, with in vitro activity at least 2-fold as that of rhG-CSF on a molar basis. It is discovered according to this invention that an added peptide linker present between hG-CSF and a human IgG Fc variant enhances the in vitro biological activity of the hG-CSF-L-Fc molecule in two ways: (1) keeping the Fc region away from the G-CSF-Rc binding sites on G-CSF, and (2) keeping one G-CSF from the other G-CSF domain, so both G-CSF domains can interact with G-CSF-Rc on the granulocyte precursor cells independently. For the present invention, a flexible peptide linker of about 20 or fewer amino acids in length is preferred. More preferably, the peptide linker should have at least two amino acids in length. Furthermore, it is even more preferable to use a peptide linker comprising two or more of the following amino acids: glycine, serine, alanine, and threonine.

The Fc region of human immunoglobulins plays a significant role in immune defense for the elimination of pathogens. Effector functions of IgG are mediated by the Fc region through two major mechanisms: (1) binding to the cell surface Fc receptors (Fc$_\gamma$Rs) can lead to ingestion of pathogens by phagocytosis or lysis by killer cells via the antibody-dependent cellular cytotoxicity (ADCC) pathway, or (2) binding to the C1q part of the first complement component C1 initiates the complement-dependent cytotoxicity (CDC) pathway, resulting in the lysis of pathogens. Among the four human IgG isotypes, IgG1 and IgG3 are effective in binding to Fc$_\gamma$R. The binding affinity of IgG4 to Fc$_\gamma$R is an order of magnitude lower than that of IgG1 or IgG3, while binding of IgG2 to Fc$_\gamma$R is below detection. Human IgG1 and IgG3 are also effective in binding to C1q and activating the complement cascade. Human IgG2 fixes complement poorly, and IgG4 appears quite deficient in the ability to activate the complement cascade (see, for example, Jefferis et al., *Immunol. Rev.*, 163:59–76, 1998). For therapeutic use in humans, it is essential that when hG-CSF-L-Fc binds to G-CSF-Rc on the surface of the progenitor cells or other cells of the myeloid lineage, the Fc region of the fusion protein will not mediate undesirable effector functions, leading to the lysis or removal of these cells. Accordingly, the Fc region of hG-CSF-L-Fc must be of a non-lytic nature, i.e. the Fc region must be inert in terms of binding to $Fc_{\gamma}Rs$ and C1q for the triggering of effector functions. It is clear that none of the naturally occurring IgG isotypes is suitable for use to produce the hG-CSF-L-Fc fusion protein. To obtain a non-lytic Fc, certain amino acids of the natural Fc region have to be mutated for the attenuation of the effector functions.

By comparing amino acid sequences of human and murine IgG isotypes, a portion of Fc near the N-terminal end of the CH2 domain is implicated to play a role in the binding of IgG Fc to $Fc_{\gamma}Rs$. The importance of a motif at positions 234 to 237 has been demonstrated using genetically engineered antibodies (see, for example, Duncan et al., *Nature*, 332:563–564, 1988). The numbering of the amino acid residues is according to the EU index as described in Kabat et al. (in *Sequences of Proteins of Immunological Interest*, $5^{th}$ Edition, United States Department of Health and Human Services, 1991). Among the four human IgG isotypes, IgG1 and IgG3 bind $Fc_{\gamma}Rs$ the best and share the sequence Leu234-Leu-Gly-Gly237 (only IgG1 is shown in FIG. 1). In IgG4, which binds $Fc_{\gamma}Rs$ with a lower affinity, this sequence contains a single amino acid substitution, Phe for Leu at position 234. In IgG2, which does not bind $Fc_{\gamma}Rs$, there are two substitutions and a deletion leading to Val234-Ala-Gly237 (FIG. 1). To minimize the binding of Fc to $Fc_{\gamma}R$ and hence the ADCC activity, Leu235 in IgG4 has been replaced by Ala (see, for example, Hutchins et al., *Proc. Natl. Acad. Sci. USA*, 92:11980–11984, 1995). IgG1 has been altered in this motif by replacing Glu233-Leu-Leu235 with Pro233-Val-Ala235, which is the sequence from IgG2. This substitution resulted in an IgG1 variant devoid of $Fc_{\gamma}R$-mediated ability to deplete target cells in mice (see, for example, Isaacs et al., *J. Immunol.*, 161:3862–3869, 1998).

A second portion that appears to be important for both $Fc_{\gamma}R$ and C1q binding is located near the carboxyl-terminal end of CH2 domain of human IgG (see, for example, Duncan et al., *Nature*, 332:738–740, 1988). Among the four human IgG isotypes, there is only one site within this portion that shows substitutions: Ser330 and Ser331 in IgG4 replacing Ala330 and Pro331 present in IgG1, IgG2, and IgG3 (FIG. 1). The presence of Ser330 does not affect the binding to $Fc_{\gamma}R$ or C1q. The replacement of Pro331 in IgG1 by Ser virtually abolished IgG1 ability to C1q binding, while the replacement of Ser331 by Pro partially restored the complement fixation activity of IgG4 (see, for example, Tao et al., *J. Exp. Med.*, 178:661–667, 1993; Xu et al., *J. Biol. Chem.*, 269:3469–3474, 1994).

We discover that at least three Fc variants (vFc) can be designed and/or used for the production of hG-CSF-L-vFc fusion proteins (FIG. 1). Human IgG2 Fc does not bind $Fc_{\gamma}R$ but showed weak complement activity. An $Fc_{\gamma2}$ variant with Pro331 Ser mutation should have less complement activity than natural $Fc_{\gamma2}$ while remain as a non-binder to $Fc_{\gamma}R$. IgG4 Fc is deficient in activating the complement cascade, and its binding affinity to $Fc_{\gamma}R$ is about an order of magnitude lower than that of the most active isotype, IgG1. An $Fc_{\gamma4}$ variant with Leu235Ala mutation should exhibit minimal effector functions as compared to the natural $Fc_{\gamma4}$. The $Fc_{\gamma1}$ variant with Leu234Val, Leu235Ala and Pro331Ser mutations also will exhibit much less effector functions than the natural $Fc_{\gamma1}$. These Fc variants are more suitable for the preparation of the G-CSF fusion proteins than naturally occurring human IgG Fc. It is possible that other replacements can be introduced for the preparation of a non-lytic Fc without compromising the circulating half-life or causing any undesirable conformational changes.

There are many advantages with the present invention. The increased activity and prolonged presence of the hG-CSF-L-vFc fusion protein in the serum can lead to lower dosages as well as less frequent injections. Less fluctuations of the drug in serum concentrations also means improved safety and tolerability. Less frequent injections may result in better patient compliance and quality of life. The hG-CSF-L-vFc fusion protein containing a non-lytic Fc variant will therefore contribute significantly to the management of a variety of conditions associated with an impaired immune or hematopoietic system, including cancer chemotherapy, leukemias, anemias AIDS, bone marrow transplantation, and chronic neutropenias.

SUMMARY OF THE INVENTION

One aspect of the present invention relates to an hG-CSF-L-vFc fusion protein. This hG-CSF-L-vFc fusion protein comprises hG-CSF, a peptide linker (denoted by L), and a human IgG Fc variant (denoted by vFc). It is preferable to use a flexible peptide linker of about 20 or fewer, more preferably to about 2, amino acids in length and the flexible peptide linker contains or comprises of two or more of amino acids selected from the group consisting of glycine, serine, alanine, and threonine. The IgG Fc variant is of non-lytic nature and contains amino acid mutations as compared to naturally occurring IgG Fc.

It is another embodiment of the present invention that the human Ig Fc comprises a hinge, CH2, and CH3 domains of human IgG, such as human IgG1, IgG2, and IgG4. The CH2 domain contains amino acid mutations at positions 228, 234, 235, and 331 (defined by the EU numbering system). It is believed that these amino acid mutations serve to attenuate the effector functions of Fc.

In yet another embodiment of the present invention, a method is disclosed for making or producing such recombinant fusion proteins from a mammalian cell line such as a CHO-derived cell line. Growing transfected cell lines under conditions such that the recombinant fusion protein is expressed in its growth medium in excess of 10, preferably 30, $\mu g$ per million cells in a 24 hour period. These hG-CSF-L-vFc fusion proteins are characterized by and exhibit increased/enhanced biological activity, preferably at least two fold (2×) in vitro activity, on a molar basis, relative to that of rhG-CSF and extended serum half-life without undesirable side effects, leading to improved pharmacokinetics and pharmacodynamics, thus lower dosages and fewer injections would be needed to achieve similar efficacies.

A further embodiment of the present invention provides a method for making a recombinant fusion protein comprising hG-CSF, a flexible peptide linker, and a human IgG Fc variant, which method comprises: (a) generating a CHO-derived cell line; (b) growing the cell line under conditions the recombinant fusion protein is expressed in its growth medium in excess of 10 µg, preferably 30 µg, per million ($10^6$) cells in a 24 hour period; and (c) purifying the expressed protein from step (b), wherein the recombinant fusion protein is characterized by and exhibits an enhanced in vitro biological activity of at least 2 fold (2x) relative to that of rhG-CSF on a molar basis. In this case, preferably, the flexible peptide linker containing or comprising about 20 or fewer, but not fewer than 2, amino acids is present between hG-CSF and the human IgG Fc variant; and the flexible peptide linker comprises two or more amino acids selected from the group consisting of glycine, serine, alanine, and threonine; and wherein the human IgG Fc variant comprises a hinge, CH2, and CH3 domains selected from the group consisting of human IgG2 with Pro331Ser mutation, human IgG4 with Ser228Pro and Leu235Ala mutations, and human IgG1 with Leu234Val, Leu235Ala, and Pro331Ser mutations.

BRIEF DESCRIPTIONS OF THE DRAWINGS

FIG. 1 shows the amino acid sequence alignment from the hinge and CH2 regions of human IgG1, IgG2, IgG4 and their variants. Three portions are compared: amino acid position 228, 234–237, and 330–331. Amino acid mutations of the variants are indicated in bold italics. The EU numbering system is used for the amino acid residues.

FIG. 2 shows the nucleotide sequence and deduced amino acid sequence of (A) hG-CSF-L-vFc$_{\gamma2}$, (B) hG-CSF-L-vFc$_{\gamma4}$, and (C) hG-CSF-L-vFc$_{\gamma1}$ as the HindIII-EcoRI fragment in the respective phGFP expression vector. Amino acid residues –30 to –1 is the leader peptide of human G-CSF. The mature protein contains human G-CSF (amino acid residues 1 to 174), a peptide linker (amino acid residues 175 to 190), and a Fc variant (amino acid residues 191 to 418 of vFc$_{\gamma2}$, 191 to 419 of vFc$_{\gamma4}$, and 191 to 417 of vFc$_{\gamma1}$). In the Fc regions, nucleotide and corresponding amino acid mutations in bold are also underlined.

DETAILED DESCRIPTION OF THE INVENTION

1. Construction of the Gene Encoding the hG-CSF-L-vFc$_{\gamma2}$ Fusion Protein A fusion protein is assembled from several DNA segments. The gene encoding the leader peptide and mature protein of human G-CSF is obtained by reverse transcription and polymerase chain reaction (PCR) using RNA prepared from the human bladder carcinoma 5637 cell line. For the convenience of cloning, SEQ ID NO:1 (Table 1), which incorporates a restriction enzyme cleavage site (HindIII) is used as the 5' oligonucleotide primer. Table 1 shows the sequences of oligonucleotides used for the cloning of the hG-CSF-L-vFc fusion proteins. The 3' primer (SEQ ID NO:2) eliminates the G-CSF termination codon and incorporates a BamHI site. The resulting DNA fragments of approximately 600 bp in length are inserted into a holding vector such as pUC19 at the HindIII and BamHI sites to give the phGCSF plasmid. The sequence of the human G-CSF gene is confirmed by DNA sequencing.

The gene encoding the Fc region of human IgG2 (Fc$_{\gamma2}$) is obtained by reverse transcription and PCR using RNA prepared from human leukocytes and appropriate 5' (SEQ ID NO:3) and 3' (SEQ ID NO:4) primers. Resulting DNA fragments of Fc$_{\gamma2}$ containing complete sequences of the hinge, CH2, and CH3 domains of IgG2 will be used as the template to generate the Fc$_{\gamma2}$ Pro331Ser variant (vFc$_{\gamma2}$) in which Pro at position 331 of Fc$_{\gamma2}$ is replaced with Ser. To incorporate this mutation, two segments are produced and then assembled by using the natural Fc$_{\gamma2}$ as the template in overlapping PCR. The 5' segment is generated by using SEQ ID NO:3 as the 5' primer and SEQ ID NO:5 as the 3' primer. The 3' segment is generated by using SEQ ID NO:6 as the 5' primer and SEQ ID NO:4 as the 3' primer. These two segments are then joined at the region covering the Pro331Ser mutation by using SEQ ID NO:7 as the 5' primer and SEQ ID NO:4 as the 3' primer. The SEQ ID NO:7 primer contains sequences encoding a 16-amino acid Gly-Ser peptide linker including a BamHI restriction enzyme site. The resulting DNA fragments of approximately 700 bp in length are inserted into a holding vector such as pUC19 at the BamHI and EcoRI sites to give the pL-vFcγ2 plasmid. The sequence of the gene is confirmed by DNA sequencing.

To prepare the hG-CSF-L-vFc$_{\gamma2}$ fusion gene, the hG-CSF fragment is excised from the phGCSF plasmid with HindIII and BamHI and is purified by agarose gel electrophoresis. The purified fragment is then inserted to the 5'-end of the peptide linker in the pL-vFcγ2 plasmid to give the phG-CSF-L-vFcγ2 plasmid. The fusion gene comprises hG-CSF, a Gly-Ser peptide linker and the Fc$_{\gamma2}$ variant gene.

The presence of a peptide linker, preferably a flexible linker, between (and chemically bound to both) the hG-CSF and Fc moieties increases the flexibility of the hG-CSF domains and enhances its biological activity. For the present invention, a peptide linker of about 20 or fewer amino acids in length is preferred. While a single amino acid is within the scope of the present invention, it is preferred to have a flexible peptide linker of about 20 to about 2 amino acids in length. Peptide linker containing or comprising of two or more of amino acids selected from the group consisting of glycine, serine, alanine, and threonine can be used preferably. An example of the peptide linker contains Gly-Ser peptide building blocks, such as GlyGlyGlyGlySer. FIG. 2A shows a fusion gene containing sequences encoding hG-CSF, a 16-amino acid peptide linker (GlySerGlyGlyGlySerGlyGlyGlySerGlyGlyGlyGlySer, SEQ ID NO: 23), and the Fc$_{\gamma2}$ Pro331Ser variant, and its corresponding amino acid sequence (SEQ ID NO: 18).

The complete gene encoding the hG-CSF-L-vFc fusion protein is then inserted at the HindIII and EcoRI sites of a mammalian expression vector, such as pcDNA3 (Invitrogen). The final expression vector plasmid, named phGFP2, contains the cytomegalovirus early gene promoter-enhancer that is required for high level expression in mammalian cells. The plasmid also contains selectable markers to confer ampicillin resistance in bacteria, and G418 resistance in mammalian cells. In addition, the phGFP2 expression vector contains the dihydrofolate reductase (DHFR) gene to enable the co-amplification of the hG-CSF-L-vFcγ2 fusion gene and the DHFR gene in the presence of methotrexate (MTX) when the host cells are deficient in the DHFR gene expression (see, for example, U.S. Pat. No. 4,399,216).

2. Construction of the Gene Encoding the hG-CSF-L-vFc$_{\gamma4}$ Fusion Protein Human IgG4 is observed partly as half antibody molecules due to the dissociation of the inter-heavy chain disulfide bonds in the hinge domain. This is not seen in the other three human IgG isotypes. A single amino acid substitution replacing Ser228 with Pro, which is the residue found at this position in IgG1 and IgG2, leads to the formation of IgG4 complete antibody molecules (see, for example, Angal et al., *Molec. Immunol.*, 30:105–108, 1993; Owens et al., *Immunotechnology*, 3:107–116, 1997; U.S. Pat. No. 6,204,007). The $Fc_{\gamma 4}$ variant containing Leu235Ala mutation for the minimization of FcR binding will also give rise to a homogeneous fusion protein preparation with this additional Ser228Pro mutation.

The gene encoding the Fc region of human IgG4 ($Fc_{\gamma 4}$) is obtained by reverse transcription and PCR using RNA prepared from human leukocytes and appropriate 5' primer (SEQ ID NO:8) and 3' primer (SEQ ID NO:9). Resulting DNA fragments of $Fc_{\gamma 4}$ containing complete sequences of the hinge, CH2, and CH3 domains of IgG4 is used as the template to generate the $Fc_{\gamma 4}$ variant with Ser228Pro and Leu235Ala mutations ($vFc_{\gamma 4}$) in which Ser228 and Leu235 have been replaced with Pro and Ala, respectively. The CH2 and CH3 domains are amplified using the 3' primer (SEQ ID NO:9) and a 5' primer containing the Leu235Ala mutation (SEQ ID NO: 10). This amplified fragment, together with a synthetic oligonucleotide of 60 bases in length (SED ID NO:11) containing both Ser228Pro and Leu235Ala mutations, are joined in PCR by using SEQ ID NO:12 as the 5' primer and SEQ ID NO:9 as the 3' primer. The SEQ ID NO:12 primer contains sequences encoding a 16-amino acid Gly-Ser peptide linker including the BamHI site. The resulting DNA fragments of approximately 700 bp in length are inserted into a holding vector such as pUC19 at the BamHI and EcoRI sites to give the pL-vFcγ4 plasmid. The sequence of the gene is confirmed by DNA sequencing.

To prepare the hG-CSF-L-$vFc_{\gamma 4}$ fusion gene, the hG-CSF fragment is excised from the phGCSF plasmid with HindIII and BamHI and then inserted to the 5'-end of the peptide linker in the pL-$vFc_{\gamma 4}$ plasmid to give the phG-CSF-L-vFcγ4 plasmid. This fusion gene comprising hG-CSF, a 16-amino acid Gly-Ser peptide linker and the $Fc_{\gamma 4}$ variant gene is then inserted at the HindIII and EcoRI sites of a mammalian expression vector, such as pcDNA3 (Invitrogen), as described for the hG-CSF-L-$vFc_{\gamma 2}$ fusion protein. The final expression vector plasmid is designated as phGFP4. FIG. 2B shows a fusion gene containing sequences encoding hG-CSF, a 16-amino acid peptide linker (GlySerGlyGlyGlySerGlyGlyGlyGlySerGlyGlyGlyGlySer, SEQ ID NO: 23), and the $Fc_{\gamma 4}$ variant with Ser228Pro and Leu235Ala mutations, and its corresponding amino acid sequence (SEQ ID NO: 20).

2. Construction of the Gene Encoding the hG-CSF-L-$vFc_{\gamma 1}$ Fusion Protein The hinge domain of human IgG1 heavy chain contains 15 amino acid residues (GluProLysSerCysAspLys-ThrHisThrCysProProCysPro, SEQ ID NO: 24) including 3 cysteine residues. Out of these 3 cysteine residues, the $2^{nd}$ and $3^{rd}$ are involved in the formation of disulfide bonding between two heavy chains. The $1^{st}$ cysteine residue is involved in the disulfide bonding to the light chain of IgG. Since there is no light chain present in the Fc fusion protein molecule, this cysteine residue may pair with other cysteine residues, leading to nonspecific disulfide bonding. The hinge domain of $Fc_{\gamma 1}$ can be truncated to eliminate the $1^{st}$ cysteine residue (AspLysThrHisThrCysProProCysPro, SEQ ID NO: 25). The gene encoding the $Fc_{\gamma 1}$ region is obtained by reverse transcription and PCR using RNA prepared from human leukocytes and appropriate 5' primer (SEQ ID NO:13) and 3' primer (SEQ ID NO:4). Resulting DNA fragments containing the truncated hinge and complete sequences of CH2 and CH3 domains of $Fc_{\gamma 1}$ is used as the template to generate the $Fc_{\gamma 1}$ variant with Leu234Val, Leu235Ala, and Pro331Ser mutations ($vFc_{\gamma 1}$), and its corresponding amino acid sequence (SEQ ID NO: 22).

One way to incorporate these mutations is as follows: two segments are produced and then assembled by using the natural $Fc_{\gamma 1}$ as the template in overlapping PCR, The 5' segment is generated by using SEQ ID NO:14 as the 5' primer and SEQ ID NO:5 as the 3' primer. This 5' primer contains the Leu234Val, Leu235Ala mutations and the 3' primer contains the Pro331Ser mutation. The 3' segment is generated by using SEQ ID NO:6 as the 5' primer and SEQ ID NO:4 as the 3' primer. These 5' and 3' segments are then joined at the region covering the Pro331Ser mutation by using SEQ ID NO:14 as the 5' primer and SEQ ID NO:4 as the 3' primer. This amplified fragment of approximately 650 bp in length, together with a synthetic oligonucleotide of 55 bases (SEQ ID NO:15) containing Leu234Val and Leu235Ala, are joined in PCR by using SEQ ID NO:16 as the 5' primer and SEQ ID NO:4 as the 3' primer. The SEQ ID NO:16 primer contains sequences encoding a 16-amino acid Gly-Ser peptide linker including the BamHI site. The resulting DNA fragments of approximately 700 bp in length are inserted into a holding vector such as pUC19 at the BamHI and EcoRI sites to give the pL-vFcγ1 plasmid. The sequence of the gene is confirmed by DNA sequencing.

To prepare the hG-CSF-L-$vFc_{\gamma 1}$ fusion gene, the hG-CSF fragment is excised from the phGCSF plasmid with HindIII and BamHI and inserted to the 5'-end of the peptide linker in the pL-vFcγ1 plasmid to give the phG-CSF-L-vFcγ1 plasmid. The fusion gene comprising hG-CSF, a 16-amino acid Gly-Ser peptide linker, and the $Fc_{\gamma 1}$ variant gene is then inserted at the HindIII and EcoRI sites of a mammalian expression vector, such as pcDNA3 (Invitrogen), as described for the hG-CSF-L-$vFc_{\gamma 2}$ fusion protein. The final expression vector plasmid is designated as phGFP1. FIG. 2C shows a fusion gene containing sequences encoding hG-CSF, a 16-amino acid peptide linker (GlySerGlyGlyGlySerGlyGlyGlyGlySerGlyGlyGlyGlySer, SEQ ID NO: 23), and the $Fc_{\gamma 1}$ variant with Leu234Val, Leu235Ala and Pro331Ser mutations), and its corresponding amino acid sequence (SEQ ID NO: 22).

3. Expression of the Fusion Protein in Transfected Cell Lines

4. Expression of the Fusion Protein in Transfected Cell Lines

Two different rhG-CSF have been produced: a glycosylated form produced in Chinese Hamster Ovary (CHO) cells and a nonglycosylated form produced in bacteirial cells. Glycosylated rhG-CSF contains O-linked oligosaccharides attached to the threonine amino acid residue at position 133, accounting for approximately 4% of its molecular weight. The carbohydrate chain contributes to the stabilization of the protein molecule by suppressing polymerization and conformational changes (Oh-eda et al., *J. Biol. Chem.*, 265:11432–11435, 1990). In in vitro studies using rhG-CSF, the glycosylated form produced in CHO cells is biologically more active than the nonglycosylated form produced in bacteirial cells (Nissen, *Eur. J. Cancer*, 30A Suppl 3:S12–S14, 1994). Furthermore, rhG-CSF derived from CHO cells was shown to be indistinguishable from its natural counterpart in terms of structural characteristics and biological activity (Kubota et al., *Biochem*.(Tokyo), 107:486–492, 1990). In randomized crossover studies in healthy volunteers, glycosylated rhG-CSF has been found to be 25 to 30% more potent than the nonglycosylated rhG-CSF on a weight for weight basis in the mobilization of peripheral blood progenitor cells (see, for example, Hoglund, *Med. Oncol.*, 15:229–233, 1998; Hoglund et al., *Eur. J. Haematol.*, 59:177–183, 1997). To obtain the protein most suitable for clinical use, the hG-CSF-L-vFc fusion protein will be produced in CHO cells as follows.

The recombinant phGFP1, phGFP2 or phGFP4 expression vector plasmid is transfected into a mammalian host cell line to achieve the expression of the hG-CSF-L-vFc fusion protein. For stable high levels of expression, a preferred host cell line is CHO cells deficient in the DHUFR enzyme (see, for example, U.S. Pat. No. 4,818,679). A preferred method of transfection is electroporation. Other methods, including calcium phosphate co-precipitation, lipofectin, and protoplast fusion, can also be used. For electroporation, 10 μg of plasmid DNA linearized with BspCI is added to 2 to $5\times10^7$ cells in a cuvette using Gene Pulser Electroporator (Bio-Rad Laboratories, Hercules, Calif.) set at an electric field of 250 V and a capacitance of 960 μFd. Two days following the transfection, the media are replaced with growth media containing 0.8 mg/ml of G418. Transfectants resistant to the selection drug are tested for the secretion of the fusion protein by anti-human IgG Fc ELISA. Quantitation of the expressed fusion protein can also be carried out by ELISA using anti-hG-CSF assays. The wells producing high levels of the Fc fusion protein are subcloned by limiting dilutions on 96-well tissue culture plates.

To achieve higher levels of the fusion protein expression, co-amplification is preferred by utilizing the gene of DHFR that can be inhibited by the MTX drug. In growth media containing increasing concentrations of MTX, the transfected fusion protein gene is co-amplified with the DHFR gene. Transfectants capable of growing in media with up to 1 μg/ml of MTX are again subcloned by limiting dilutions. The subcloned cell lines are further analyzed by measuring the secretion rates. Several cell lines yielding secretion rate levels over about 10, preferably about 30 μg/$10^6$ [i.e. million]cells/24 h, are adapted to suspension culture using serum-free growth media. The conditioned media are then used for the purification of the fusion protein.

5. Purification and Characterization of the Fusion Protein

Conditioned media containing the fusion protein are titrated with 1 N NaOH to a pH of 7 to 8 and filtered through a 0.45 micron cellulose nitrate filter. The filtrate is loaded onto a Prosep A column equilibrated in phospate-buffered saline (PBS). After binding of the fusion protein to Prosep A, the flow-through fractions are discarded. The column is washed with PBS until OD at 280 nm is below 0.01. The bound fusion protein is then eluted with 0.1 M citrate buffer at pH 3.75. After neutralizing with 0.4 volume of 1 M $K_2HPO_4$, fractions containing purified protein are pooled and dialyzed against PBS. The solution is then filtered through a 0.22 micron cellulose nitrate filter and stored at 4° C. The molecular weight of purified hG-CSF-L-vFc protein is in the range of 90 and 110 kDa by SDS-PAGE under non-reducing conditions. Under reducing conditions, the purified protein migrates around approximately 50 kDa. The fusion protein is quantitated by BCA protein assay using BSA as the standard.

6. In vitro Biological Assays

Supernatants of transfectants or purified proteins can be tested for their ability to stimulate the proliferation of murine myeloblastic NFS-60 cells (Shirafuji et al., *Exp. Hematol.*, 17:116–119, 1989). NFS-60 cells are responsive to rhG-CSF but not to rhGM-CSF or hM-CSF. The cells are maintained in growth medium (RPMI-1640 medium containing 10% FCS and murine IL-3 at 1 ng/ml). Log phase NFS-60 cells are collected and washed with assay medium (growth medium without murine IL-3). A total of $1\times10^4$ cells per sample of NFS-60 in 50 μl is added to each well of a 96-well tissue culture plate. The cells are incubated with 50 μl of assay media containing various concentrations of the hG-CSF-L-vFc fusion protein or the rhG-CSF control from 0.01 to 100 nM each. The plate is kept at 37° C. and 5% $CO_2$ in a humidified incubator for 4 days before 10 μl of MTT (2.5 mg/ml in PBS) is added to each well. After 4 h, the cells and formazan are solubilized by adding 100 μl per well of 10% SDS in 0.01 N HCl. The plate is then read at 550 nm with the reference beam set at 690 nm. The OD reading is plotted against the concentration of rhG-CSF or the fusion protein. The inflection point of the sigmoidal curve represents the concentration at which 50% of the maximal effect, ED50, is induced. The biological activity of hG-CSF-L-vFc relative to that of rhG-CSF can therefore be compared quantitatively. Preferably, the recombinant fusion proteins should be characterized by and exhibit an enhanced activity of at least 2 fold (2×) relative to that of rhG-CSF on a molar basis. In one embodiment of the present invention, the specific activity of the hG-CSF-L-vFc fusion protein is in the range of about 1.5 to about $6.0\times10^9$ units/μmole, compared to about 0.75 to about $3.0\times10^9$ units/μmole for rhG-CSF based on this cell proliferation assay.

Supernatants of transfectants or purified proteins can also be tested for their ability to stimulate the proliferation and differentiation of human bone marrow progenitor cells to form colonies, granulocyte-macrophage colony forming unit (CFU-GM). The procedure is as follows. Light-density cells from human bone marrow centrifuged over Ficoll-Pague are washed and resuspended at $1\times10^6$ cells/ml in Iscove's modified Dulbecco's medium (IMDM) containing 5% FCS. These cells containing enriched progenitor cells are incubated in a tissue culture dish overnight at 37° C. and 5% $CO_2$ to remove all adherent cells including monocytes, macrophages, endothelial cell, and fibroblasts. Cells in suspension are then adjusted to $1\times10^5$ cells/ml in IMDM containing 5% FCS. For the assay, 0.3 ml of cells, 15 μl of stem cell factor at 20 μg/ml, 2.4 ml of methylcellulose, and 0.3 ml of media containing several concentrations of hG-CSF-L-vFc (or rhG-CSF control) are mixed. One ml of this cell mixture is plated on a 35-mm petri dish. The dishes are then kept at 37° C. and 5% $CO_2$ for 10 to 14 d before the colonies are counted. A dose responsive curve can be plotted against the concentrations of hG-CSF-L-vFc relative to those of rhG-CSF.

7. In vivo Pharmacokinetic Studies in Rats

Fisher rats (Harlan Bioproducts for Science, Indianapolis, Ind.) with an average body weight of about 500 g are injected i.v. through the tail vein or s.c. with 100 units of rhG-CSF or the hG-CSF-L-vFc fusion protein. An equal volume of PBS is injected as a control. Serial 0.5-ml samples are taken through retro-orbital bleeds at different points (0, 0.2, 1, 4, 24, 48, 96, and 168 h) after injection. There are 3 rats for each time point. Whole blood is collected into tubes containing anticoagulant, cells are removed, and plasma is frozen at −70° C. until assay is carried out.

Serum samples are used for NFS-60 cell assays, which measure the activity of hG-CSF-mediated cell proliferation. A total of $1\times10^4$ cells per sample of NFS-60 in 50 μl is added to each well of a 96-well tissue culture plate. The cells are incubated with 50 μl of assay media containing various concentrations of titrated blood samples. The plate is kept at 37° C. and 5% $CO_2$ in a humidified incubator for 4 days. Viable cells are stained with 10 μl of MTT (2.5 mg/ml in PBS). After 4 h, the cells and formazan are solubilized by adding 100 μl per well of 10% SDS in 0.01 N HCl. The plate is then read at 550 nm with the reference beam set at 690 nm. The activities of serum samples are plotted against time points for the calculation of the circulation time. The activity of hG-CSF-L-vFc decreases much slower than that of the rhG-CSF control, indicating the longer circulating half-life of the fusion protein in rats.

The examples described above are for illustration purposes only. They are not intended and should not be interpreted to limit either the scope or the spirit of this invention. It can be appreciated by those skilled in the art that many other variations or substitutes can be used as equivalents for the purposes of this invention, which is defined solely by the written description and the following claims.

TABLE 1

Sequences of Oligonucleotides.

SEQ ID NO:1
5'-cccaagcttcccagacccatggctggacct-3'

SEQ ID NO:2
5'-cggatccgggctgggcaaggtggcgta-3'

SEQ ID NO:3
5'-gagcgcaaatgttgtgtcga-3'

SEQ ID NO:4
5'-ggaattctcatttacccggagacaggga-3'

SEQ ID NO:5
5'-tggttttctcgatggaggctgggaggcct-3'

SEQ ID NO:6
5'-aggcctcccagcctccatcgagaaaacca-3'

SEQ ID NO:7
5'-cggatccggtggcggttccggtggaggcggaagcggcggtggaggat
cagagcgcaaatgttgtgtcga-3'

SEQ ID NO:8
5'-gagtccaaatatggtcccca-3'

TABLE 1-continued

Sequences of Oligonucleotides.

SEQ ID NO:9
5'-ggaattctcatttacccagagacaggga-3'

SEQ ID NO:10
5'-cctgagttcgcgggggggacca-3'

SEQ ID NO:11
5'-gagtccaaatatggtcccccatgcccaccatgcccagcacctgagtt
cgcgggggacca-3'

SEQ ID NO:12
5'-cggatccggtggcggttccggtggaggcggaagcggcggtggaggat
cagagtccaaatatggtccccca-3'

SEQ ID NO:13
5'-gacaaaactcacacatgccca-3'

SEQ ID NO:14
5'-acctgaagtcgcgggggggaccgt-3'

SEQ ID NO:15
5'-gacaaaactcacacatgcccaccgtgcccagcacctgaagtcgcggg
gggaccgt-3'

SEQ ID NO:16
5'-cggatccggtggcggttccggtggaggcggaagcggcggtggaggat
cagacaaaactcacacatgccca-3'

What is claimed is:

1. A recombinant hG-CSF-L-vFc fusion protein comprising hG-CSF, a peptide linker, and a human IgG Fc variant, wherein the human IgF Fc variant comprises a hinge, CH2, and CH3 domains of human IgG2 with Pro331Ser mutation as SEQ ID NO 18.

2. The recombinant hG-CSF-L-vFc fusion protein of claim 1, wherein the peptide linker (i) comprises about 20 or fewer amino acids; (ii) is present between hG-CSF and the human IgG Fc variant; and (iii) comprises two or more amino acids selected from the group consisting of glycine, serine, alanine, and threonine.

3. The recombinant hG-CSF-L-vFc fusion protein of claim 1, wherein the hG-CSF-L-vFc fusion protein is characterized by an enhanced in vitro biological activity of at least 2 fold relative to that of rhG-CSF on a molar basis.

4. A CHO-derived cell line producing the hG-CSF-L-vFc fusion protein of claim 1 in the cell line's growth medium in excess of 10 μg per million cells in a 24 hour period.

5. The CHO-derived cell line producing the hG-CSF-L-vFc fushion protein of claim 4 in the cell line's growth medium in excess of 30 μg per million cells in a 24 hour period.

6. A method for making a recombinant fusion protein comprising hG-CSF, a flexible peptide linker, and a human IgG Fc variant, which method comprises:

(a) generating a CHO-derived cell line by transforming the CHO cell line with a gene encoding the recombinant fusion protein comprising hG-CSF; (b) growing the cell line under conditions sufficient for expressing the recombinant fusion protein in the cell line's growth medium at a rate of in excess of 10 μg per million cells in a 24 hour period; and (c) purifying the expressed protein from step (b), wherein the recombinant fusion protein is characterized by an enhanced in vitro biological activity of at least 2 fold relative to that of rhG-CSF on a molar basis; and wherein the human IgG Fc variant comprises a hinge, CH2, and CH3 domains of human IgG2 with Pro331Ser mutation as SEQ ID NO 18.

7. The method of claim 6, wherein in step (b) growing the cell line under conditions sufficient for expressing the recombinant fusion protein in the cell line's growth medium at a rate of in excess of 30 μg per million cells in a 24 hour period.

8. The method of claim 6, wherein the flexible peptide linker (i) comprises about 20 or fewer amino acids; (ii) is present between hG-CSF and the human IgG Fc variant; and (iii) comprises two or more amino acids selected from the group consisting of glycine, serine, alanine, and threonine.

9. The method of claim 8, wherein in step (b) growing the cell line under conditions sufficient for expressing the recombinant fusion protein in the cell line's growth medium at a rate of in excess of 30 μg per million cells in a 24 hour period.

10. The method of claim 6, wherein the human IgG Fc variant comprises a hinge, CH2, and CH3 domains of human IgG2 with Pro331Ser mutation as SEQ ID NO 18.

11. The method of claim 10, wherein in step (b) growing the cell line under conditions sufficient for expressing the recombinant fusion protein in the cell line's growth medium at a rate of in excess of 30 μg per million cells in a 24 hour period.

12. A method for making a recombinant fusion protein comprising hG-CSF, a flexible peptide linker, and a human IgG Fc variant, which method comprises:

(a) generating a CHO-derived cell line by transforming the CHO cell line with a gene encoding the recombinant fusion protein comprising hG-CSF; (b) growing the cell line under conditions sufficient for expressing the recombinant protein in the cell line's growth medium at rate of in excess of 10 μg per million cells in a 24 hour period; and (c) purifying the expressed protein from step (b), wherein the recombinant fusion protein is characterized by an enhanced in vitro biological activity of at least 2 fold relative to that of rhG-CSF on a molar basis; wherein the flexible peptide linker (i) comprises about 20 or fewer amino acids; (ii) is present between hG-CSF and the human IgG Fc variant; and (iii) comprises two or more amino acids selected from the group consisting of glycine, serine, alanine, and threonine; and wherein the human IgG Fc variant comprises a hinge, CH2, and CH3 domains selected from the group consisting of human IgG2 with Pro331Ser mutation as SEQ ID NO 18.

* * * * *

SEQUENCE LISTING

<160> NUMBER OF SEQ ID NOS: 28

<210> SEQ ID NO 1
<211> LENGTH: 30
<212> TYPE: DNA
<213> ORGANISM: Artificial Sequence
<220> FEATURE:
<223> OTHER INFORMATION: PCR primer

<400> SEQUENCE: 1
cccaagcttc ccagacccat ggctggacct    30

<210> SEQ ID NO 2
<211> LENGTH: 27
<212> TYPE: DNA
<213> ORGANISM: Artificial sequence
<220> FEATURE:
<223> OTHER INFORMATION: PCR primer

<400> SEQUENCE: 2
cggatccggg ctgggcaagg tggcgta    27

<210> SEQ ID NO 3
<211> LENGTH: 20
<212> TYPE: DNA
<213> ORGANISM: Artificial Sequence

```
<220> FEATURE:
<223> OTHER INFORMATION: PCR primer

<400> SEQUENCE: 3
gagcgcaaat gttgtgtcga                                               20

<210> SEQ ID NO 4
<211> LENGTH: 28
<212> TYPE: DNA
<213> ORGANISM: Artificial Sequence
<220> FEATURE:
<223> OTHER INFORMATION: PCR primer

<400> SEQUENCE: 4
ggaattctca tttacccgga gacaggga                                      28

<210> SEQ ID NO 5
<211> LENGTH: 29
<212> TYPE: DNA
<213> ORGANISM: Artificial Sequence
<220> FEATURE:
<223> OTHER INFORMATION: PCR primer

<400> SEQUENCE: 5
tggttttctc gatggaggct gggaggcct                                     29

<210> SEQ ID NO 6
<211> LENGTH: 29
<212> TYPE: DNA
<213> ORGANISM: Artificial Sequence
<220> FEATURE:
<223> OTHER INFORMATION: PCR primer

<400> SEQUENCE: 6
aggcctccca gcctccatcg agaaaacca                                     29

<210> SEQ ID NO 7
<211> LENGTH: 69
<212> TYPE: DNA
<213> ORGANISM: Artificial Sequence
<220> FEATURE:
<223> OTHER INFORMATION: PCR primer

<400> SEQUENCE: 7
cggatccggt ggcggttccg gtggaggcgg aagcggcggt ggaggatcag agcgcaaatg   60
ttgtgtcga                                                           69

<210> SEQ ID NO 8
<211> LENGTH: 21
<212> TYPE: DNA
<213> ORGANISM: Artificial Sequence
<220> FEATURE:
<223> OTHER INFORMATION: PCR primer

<400> SEQUENCE: 8
gagtccaaat atggtccccc a                                             21

<210> SEQ ID NO 9
<211> LENGTH: 28
<212> TYPE: DNA
<213> ORGANISM: Artificial Sequence
<220> FEATURE:
<223> OTHER INFORMATION: PCR primer

<400> SEQUENCE: 9
```

-continued ggaattctca tttacccaga gacaggga                                          28

<210> SEQ ID NO 10
<211> LENGTH: 21
<212> TYPE: DNA
<213> ORGANISM: Artificial Sequence
<220> FEATURE:
<223> OTHER INFORMATION: PCR primer

<400> SEQUENCE: 10
cctgagttcg cggggggacc a                                                 21

<210> SEQ ID NO 11
<211> LENGTH: 60
<212> TYPE: DNA
<213> ORGANISM: Artificial Sequence
<220> FEATURE:
<223> OTHER INFORMATION: PCR primer

<400> SEQUENCE: 11
gagtccaaat atggtccccc atgcccacca tgcccagcac ctgagttcgc gggggaccca       60

<210> SEQ ID NO 12
<211> LENGTH: 70
<212> TYPE: DNA
<213> ORGANISM: Artificial Sequence
<220> FEATURE:
<223> OTHER INFORMATION: PCR primer

<400> SEQUENCE: 12
cggatccggt ggcggttccg gtggaggcgg aagcggcggt ggaggatcag agtccaaata       60
tggtccccca                                                              70

<210> SEQ ID NO 13
<211> LENGTH: 21
<212> TYPE: DNA
<213> ORGANISM: Artificial Sequence
<220> FEATURE:
<223> OTHER INFORMATION: PCR primer

<400> SEQUENCE: 13
gacaaaactc acacatgccc a                                                 21

<210> SEQ ID NO 14
<211> LENGTH: 23
<212> TYPE: DNA
<213> ORGANISM: Artificial Sequence
<220> FEATURE:
<223> OTHER INFORMATION: PCR primer

<400> SEQUENCE: 14
acctgaagtc gcggggggac cgt                                               23

<210> SEQ ID NO 15
<211> LENGTH: 55
<212> TYPE: DNA
<213> ORGANISM: Artificial Sequence
<220> FEATURE:
<223> OTHER INFORMATION: PCR primer

<400> SEQUENCE: 15
gacaaaactc acacatgccc accgtgccca gcacctgaag tcgcgggggg accgt            55

<210> SEQ ID NO 16
<211> LENGTH: 70

<212> TYPE: DNA
<213> ORGANISM: Artificial Sequence
<220> FEATURE:
<223> OTHER INFORMATION: PCR primer

<400> SEQUENCE: 16
cggatccggt ggcggttccg gtggaggcgg aagcggcggt ggaggatcag acaaaactca    60
cacatgccca                                                           70

<210> SEQ ID NO 17
<211> LENGTH: 1368
<212> TYPE: DNA
<213> ORGANISM: Artificial Sequence
<220> FEATURE:
<223> OTHER INFORMATION: hG-CSF-L-vFc gamma2 (Figure 2A)

<400> SEQUENCE: 17
aagcttccca gacccatggc tggacctgcc acccagagcc ccatgaagct gatggccctg    60
cagctgctgc tgtggcacag tgcactctgg acagtgcagg aagccacccc cctgggccct   120
gccagctccc tgccccagag cttcctgctc aagtgcttag agcaagtgag gaagatccag   180
ggcgatggcg cagcgctcca ggagaagctg tgtgccacct acaagctgtg ccaccccgag   240
gagctggtgc tgctcggaca ctctctgggc atcccctggg ctcccctgag cagctgcccc   300
agccaggccc tgcagctggc aggctgcttg agccaactcc atagcggcct tttcctctac   360
caggggctcc tgcaggccct ggaagggatc tcccccgagt tgggtccac cttggacaca    420 ctgcagctgg acgtcgccga cttttgccacc accatctggc agcagatgga agaactggga   480
atggcccctg ccctgcagcc cacccagggt gccatgccgg ccttcgcctc tgctttccag   540
cgccgggcag gaggggtcct agttgcctcc catctgcaga gcttcctgga ggtgtcgtac   600
cgcgttctac gccaccttgc ccagcccgga tccggtggcg gttccggtgg aggcggaagc   660
ggcggtggag gatcagagcg caaatgttgt gtcgagtgcc caccgtgccc agcaccacct   720
gtggcaggac cgtcagtctt cctcttcccc caaaaccca aggacaccct catgatctcc    780
cggacccctg aggtcacgtg cgtggtggtg gacgtgagcc acgaagaccc cgaggtccag   840
ttcaactggt acgtggacgg cgtggaggtg cataatgcca agacaaagcc acgggaggag   900
cagttcaaca gcacgttccg tgtggtcagc gtcctcaccg ttgtgcacca ggactggctg   960
aacggcaagg agtacaagtg caaggtctcc aacaaggcc tcccagcctc catcgagaaa   1020
accatctcca aaaccaaagg gcagccccga gaaccacagg tgtacaccct gcccccatcc   1080
cgggaggaga tgaccaagaa ccaggtcagc ctgacctgcc tggtcaaagg cttctacccc   1140
agcgacatcg ccgtggagtg ggagagcaat gggcagccgg agaacaacta caagaccaca   1200
cctcccatgc tggactccga cggctccttc ttcctctaca gcaagctcac cgtggacaag   1260
agcaggtggc agcaggggaa cgtcttctca tgctccgtga tgcatgaggc tctgcacaac   1320
cactacacgc agaagagcct ctccctgtct ccgggtaaat gagaattc                 1368

<210> SEQ ID NO 18
<211> LENGTH: 448
<212> TYPE: PRT
<213> ORGANISM: Artificial Sequence
<220> FEATURE:
<223> OTHER INFORMATION: hG-CSF-L-vFc gamma2 with a 30-amino acid
      leader peptide (Figure 2A)

<400> SEQUENCE: 18

Met Ala Gly Pro Ala Thr Gln Ser Pro Met Lys Leu Met Ala Leu Gln

-continued

```
1               5                    10                  15
Leu Leu Leu Trp His Ser Ala Leu Trp Thr Val Gln Glu Ala Thr Pro
            20                  25                  30
Leu Gly Pro Ala Ser Ser Leu Pro Gln Ser Phe Leu Leu Lys Cys Leu
            35                  40                  45
Glu Gln Val Arg Lys Ile Gln Gly Asp Gly Ala Ala Leu Gln Glu Lys
            50                  55                  60
Leu Cys Ala Thr Tyr Lys Leu Cys His Pro Glu Glu Leu Val Leu Leu
65                      70                  75                  80
Gly His Ser Leu Gly Ile Pro Trp Ala Pro Leu Ser Ser Cys Pro Ser
                    85                  90                  95
Gln Ala Leu Gln Leu Ala Gly Cys Leu Ser Gln Leu His Ser Gly Leu
                    100                 105                 110
Phe Leu Tyr Gln Gly Leu Leu Gln Ala Leu Glu Gly Ile Ser Pro Glu
            115                 120                 125
Leu Gly Pro Thr Leu Asp Thr Leu Gln Leu Asp Val Ala Asp Phe Ala
            130                 135                 140
Thr Thr Ile Trp Gln Gln Met Glu Glu Leu Gly Met Ala Pro Ala Leu
145                     150                 155                 160
Gln Pro Thr Gln Gly Ala Met Pro Ala Phe Ala Ser Ala Phe Gln Arg
                    165                 170                 175
Arg Ala Gly Gly Val Leu Val Ala Ser His Leu Gln Ser Phe Leu Glu
                    180                 185                 190
Val Ser Tyr Arg Val Leu Arg His Leu Ala Gln Pro Gly Ser Gly Gly
            195                 200                 205
Gly Ser Gly Gly Gly Gly Ser Gly Gly Gly Gly Ser Glu Arg Lys Cys
            210                 215                 220
Cys Val Glu Cys Pro Pro Cys Pro Ala Pro Pro Val Ala Gly Pro Ser
225                     230                 235                 240
Val Phe Leu Phe Pro Pro Lys Pro Lys Asp Thr Leu Met Ile Ser Arg
                    245                 250                 255
Thr Pro Glu Val Thr Cys Val Val Val Asp Val Ser His Glu Asp Pro
                    260                 265                 270
Glu Val Gln Phe Asn Trp Tyr Val Asp Gly Val Glu Val His Asn Ala
            275                 280                 285
Lys Thr Lys Pro Arg Glu Glu Gln Phe Asn Ser Thr Phe Arg Val Val
            290                 295                 300
Ser Val Leu Thr Val Val His Gln Asp Trp Leu Asn Gly Lys Glu Tyr
305                     310                 315                 320
Lys Cys Lys Val Ser Asn Lys Gly Leu Pro Ala Ser Ile Glu Lys Thr
                    325                 330                 335
Ile Ser Lys Thr Lys Gly Gln Pro Arg Glu Pro Gln Val Tyr Thr Leu
                    340                 345                 350
Pro Pro Ser Arg Glu Glu Met Thr Lys Asn Gln Val Ser Leu Thr Cys
            355                 360                 365
Leu Val Lys Gly Phe Tyr Pro Ser Asp Ile Ala Val Glu Trp Glu Ser
            370                 375                 380
Asn Gly Gln Pro Glu Asn Asn Tyr Lys Thr Thr Pro Pro Met Leu Asp
385                     390                 395                 400
Ser Asp Gly Ser Phe Phe Leu Tyr Ser Lys Leu Thr Val Asp Lys Ser
                    405                 410                 415
Arg Trp Gln Gln Gly Asn Val Phe Ser Cys Ser Val Met His Glu Ala
                    420                 425                 430
```

Leu His Asn His Tyr Thr Gln Lys Ser Leu Ser Leu Ser Pro Gly Lys
           435                      440                  445

<210> SEQ ID NO 19
<211> LENGTH: 1371
<212> TYPE: DNA
<213> ORGANISM: Artificial Sequence
<220> FEATURE:
<223> OTHER INFORMATION: hG-CSF-L-vFc gamma4 (Figure 2B)

<400> SEQUENCE: 19

```
aagcttccca gacccatggc tggacctgcc acccagagcc ccatgaagct gatggccctg      60
cagctgctgc tgtggcacag tgcactctgg acagtgcagg aagccacccc cctgggccct     120
gccagctccc tgccccagag cttcctgctc aagtgcttag agcaagtgag gaagatccag     180
ggcgatggcg cagcgctcca ggagaagctg tgtgccacct acaagctgtg ccaccccgag     240
gagctggtgc tgctcggaca ctctctgggc atccccctggg ctcccctgag cagctgcccc     300
agccaggccc tgcagctggc aggctgcttg agccaactcc atagcggcct tttcctctac     360
cagggctcc tgcaggccct ggaagggatc tcccccgagt tgggtcccac cttggacaca     420
ctgcagctgg acgtcgccga ctttgccacc accatctggc agcagatgga agaactggga     480
atggcccctg ccctgcagcc cacccagggt gccatgccgg ccttcgcctc tgctttccag     540
cgccgggcag gagggtcct agttgcctcc catctgcaga gcttcctgga ggtgtcgtac     600
cgcgttctac gccaccttgc ccagcccgga tccggtggcg gttccggtgg aggcggaagc     660
ggcggtggag gatcagagtc caaatatggt ccccatgcc accatgccc agcacctgag     720
ttcgcggggg gaccatcagt cttcctgttc ccccaaaac ccaaggacac tctcatgatc     780
tcccggaccc ctgaggtcac gtgcgtggtg gtggacgtga gccaggaaga ccccgaggtc     840
cagttcaact ggtacgtgga tggcgtggag gtgcataatg ccaagacaaa gccgcgggag     900
gagcagttca acagcacgta ccgtgtggtc agcgtcctca ccgtcctgca ccaggactgg     960
ctgaacggca aggagtacaa gtgcaaggtc tccaacaaag gcctcccgtc tccatcgag    1020
aaaaccatct ccaaagccaa agggcagccc cgagagccac aggtgtacac cctgccccca    1080
tcccaggagg agatgaccaa gaaccaggtc agcctgacct gcctggtcaa aggcttctac    1140
cccagcgaca tcgccgtgga gtgggagagc aatgggcagc cggagaacaa ctacaagacc    1200
acgcctcccg tgctggactc cgacggctcc ttcttcctct acagcaggct aaccgtggac    1260
aagagcaggt ggcaggaggg gaatgtcttc tcatgctccg tgatgcatga ggctctgcac    1320
aaccactaca cacagaagag cctctccctg tctctgggta aatgagaatt c             1371
```

<210> SEQ ID NO 20
<211> LENGTH: 449
<212> TYPE: PRT
<213> ORGANISM: Artificial Sequence
<220> FEATURE:
<223> OTHER INFORMATION: hG-CSF-L-vFc gamma4 with a 30-amino acid
    leader peptide (Figure 2B)

<400> SEQUENCE: 20

Met Ala Gly Pro Ala Thr Gln Ser Pro Met Lys Leu Met Ala Leu Gln
1             5                10               15

Leu Leu Leu Trp His Ser Ala Leu Trp Thr Val Gln Glu Ala Thr Pro
                20                25               30

Leu Gly Pro Ala Ser Ser Leu Pro Gln Ser Phe Leu Leu Lys Cys Leu
                35                40               45

```
Glu Gln Val Arg Lys Ile Gln Gly Asp Gly Ala Ala Leu Gln Glu Lys
        50                  55                  60

Leu Cys Ala Thr Tyr Lys Leu Cys His Pro Glu Leu Val Leu Leu
65                  70                  75                  80

Gly His Ser Leu Gly Ile Pro Trp Ala Pro Leu Ser Ser Cys Pro Ser
                    85                  90                  95

Gln Ala Leu Gln Leu Ala Gly Cys Leu Ser Gln Leu His Ser Gly Leu
                100                 105                 110

Phe Leu Tyr Gln Gly Leu Leu Gln Ala Leu Glu Gly Ile Ser Pro Glu
            115                 120                 125

Leu Gly Pro Thr Leu Asp Thr Leu Gln Leu Asp Val Ala Asp Phe Ala
    130                 135                 140

Thr Thr Ile Trp Gln Gln Met Glu Glu Leu Gly Met Ala Pro Ala Leu
145                 150                 155                 160

Gln Pro Thr Gln Gly Ala Met Pro Ala Phe Ala Ser Ala Phe Gln Arg
                165                 170                 175

Arg Ala Gly Gly Val Leu Val Ala Ser His Leu Gln Ser Phe Leu Glu
            180                 185                 190

Val Ser Tyr Arg Val Leu Arg His Leu Ala Gln Pro Gly Ser Gly Gly
    195                 200                 205

Gly Ser Gly Gly Gly Gly Ser Gly Gly Gly Ser Glu Ser Lys Tyr
                210                 215                 220

Gly Pro Pro Cys Pro Pro Cys Pro Ala Pro Glu Phe Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
                275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
    355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
    435                 440                 445

Lys
```

<210> SEQ ID NO 21
<211> LENGTH: 1365
<212> TYPE: DNA
<213> ORGANISM: Artificial Sequence
<220> FEATURE:
<223> OTHER INFORMATION: hG-CSF-L-vFc gamma1 (Figure 2C)

<400> SEQUENCE: 21

```
aagcttccca gacccatggc tggacctgcc acccagagcc ccatgaagct gatggccctg      60
cagctgctgc tgtggcacag tgcactctgg acagtgcagg aagccacccc cctgggccct     120
gccagctccc tgccccagag cttcctgctc aagtgcttag agcaagtgag gaagatccag     180
ggcgatggcg cagcgctcca ggagaagctg tgtgccacct acaagctgtg ccaccccgag     240
gagctggtgc tgctcggaca ctctctgggc atcccctggg ctcccctgag cagctgcccc     300
agccaggccc tgcagctggc aggctgcttg agccaactcc atagcggcct tttcctctac     360
cagggggctcc tgcaggccct ggaagggatc tcccccgagt tgggtcccac cttggacaca     420
ctgcagctgg acgtcgccga ctttgccacc accatctggc agcagatgga agaactggga     480
atggcccctg ccctgcagcc cacccagggt gccatgccgg ccttcgcctc tgctttccag     540
cgccgggcag gagggtcct agttgcctcc catctgcaga gcttcctgga ggtgtcgtac     600
cgcgttctac gccaccttgc ccagcccgga tccggtggcg gttccggtgg aggcggaagc     660
ggcggtggag gatcagacaa aactcacaca tgcccaccgt gcccagcacc tgaagtcgcg     720
gggggaccgt cagtcttcct cttcccccca aaacccaagg acaccctcat gatctcccgg     780
acacctgagg tcacatgcgt ggtggtggac gtgagccacg aagaccctga ggtcaagttc     840
aactggtacg tggacggcgt ggaggtgcat aatgccaaga caaagccgcg ggaggagcag     900
tacaacagca cgtaccgggt ggtcagcgtc ctcaccgtcc tgcaccagga ctggctgaat     960
ggcaaggagt acaagtgcaa ggtctccaac aaagccctcc cagcctccat cgagaaaacc    1020
atctccaaag ccaagggca gccccgagaa ccacaggtgt acaccctgcc cccatcccgg    1080
gatgagctga ccaagaacca ggtcagcctg acctgcctgg tcaaaggctt ctatcccagc    1140
gacatcgccg tggagtggga gagcaatggg cagccggaga caactacaa gaccacgcct    1200
cccgtgctgg actccgacgg ctccttcttc ctctacagca agctcaccgt ggacaagagc    1260
aggtggcagc aggggaacgt cttctcatgc tccgtgatgc atgaggctct gcacaaccac    1320
tacacgcaga gagcctctc cctgtctccg ggtaaatgag aattc                     1365
```

<210> SEQ ID NO 22
<211> LENGTH: 447
<212> TYPE: PRT
<213> ORGANISM: Artificial Sequence
<220> FEATURE:
<223> OTHER INFORMATION: hG-CSF-L-vFc gamma1 with a 30-amino acid
      leader peptide (Figure 2C)

<400> SEQUENCE: 22

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Cys Ala Thr Tyr Lys Leu Cys His Pro Glu Glu Leu Val Leu Leu

```
               65                  70                  75                  80
Gly His Ser Leu Gly Ile Pro Trp Ala Pro Leu Ser Ser Cys Pro Ser
                     85                  90                  95
Gln Ala Leu Gln Leu Ala Gly Cys Leu Ser Gln Leu His Ser Gly Leu
                100                 105                 110
Phe Leu Tyr Gln Gly Leu Leu Gln Ala Leu Glu Gly Ile Ser Pro Glu
            115                 120                 125
Leu Gly Pro Thr Leu Asp Thr Leu Gln Leu Asp Val Ala Asp Phe Ala
        130                 135                 140
Thr Thr Ile Trp Gln Gln Met Glu Glu Leu Gly Met Ala Pro Ala Leu
145                 150                 155                 160
Gln Pro Thr Gln Gly Ala Met Pro Ala Phe Ala Ser Ala Phe Gln Arg
                165                 170                 175
Arg Ala Gly Gly Val Leu Val Ala Ser His Leu Gln Ser Phe Leu Glu
                180                 185                 190
Val Ser Tyr Arg Val Leu Arg His Leu Ala Gln Pro Gly Ser Gly Gly
            195                 200                 205
Gly Ser Gly Gly Gly Gly Ser Gly Gly Gly Ser Asp Lys Thr His
        210                 215                 220
Thr Cys Pro Pro Cys Pro Ala Pro Glu Val Ala Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
                260                 265                 270
Val Lys Phe Asn Trp Tyr Val Asp Gly Val Glu Val His Asn Ala Lys
            275                 280                 285
Thr Lys Pro Arg Glu Glu Gln Tyr Asn Ser Thr Tyr Arg Val Val Ser
        290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Ser Ile Glu Lys Thr Ile
                325                 330                 335
Ser Lys Ala Lys Gly Gln Pro Arg Glu Pro Gln Val Tyr Thr Leu Pro
                340                 345                 350
Pro Ser Arg Asp Glu Leu Thr Lys Asn Gln Val Ser Leu Thr Cys Leu
            355                 360                 365
Val Lys Gly Phe Tyr Pro Ser Asp Ile Ala Val Glu Trp Glu Ser Asn
        370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
                420                 425                 430
His Asn His Tyr Thr Gln Lys Ser Leu Ser Leu Ser Pro Gly Lys
            435                 440                 445

<210> SEQ ID NO 23
<211> LENGTH: 16
<212> TYPE: PRT
<213> ORGANISM: Artificial sequence
<220> FEATURE:
<223> OTHER INFORMATION: 16-amino acid peptide linker
```

```
<400> SEQUENCE: 23

Gly Ser Gly Gly Gly Ser Gly Gly Gly Ser Gly Gly Gly Gly Ser
1               5                   10                  15

<210> SEQ ID NO 24
<211> LENGTH: 15
<212> TYPE: PRT
<213> ORGANISM: Human IgG1 hinge sequence

<400> SEQUENCE: 24

Glu Pro Lys Ser Cys Asp Lys Thr His Thr Cys Pro Pro Cys Pro
1               5                   10                  15

<210> SEQ ID NO 25
<211> LENGTH: 10
<212> TYPE: PRT
<213> ORGANISM: Truncated human IgG1 hinge sequence

<400> SEQUENCE: 25

Asp Lys Thr His Thr Cys Pro Pro Cys Pro
1               5                   10

<210> SEQ ID NO 26
<211> LENGTH: 232
<212> TYPE: PRT
<213> ORGANISM: Human IgG1 Fc with native hinge, CH2 and CH3 domains

<400> SEQUENCE: 26

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 27
<211> LENGTH: 228
<212> TYPE: PRT
<213> ORGANISM: Human IgG2 Fc with native hinge, CH2 and CH3 domains

<400> SEQUENCE: 27

```
Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225
```

<210> SEQ ID NO 28
<211> LENGTH: 229
<212> TYPE: PRT
<213> ORGANISM: Human IgG4 Fc with native hinge, CH2 and CH3 domains

<400> SEQUENCE: 28

```
Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95
```

-continued

```
Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
            130                 135             140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
    210                 215                 220

Leu Ser Leu Gly Lys
225
```